United States Patent
Miller et al.

[11] Patent Number: 6,150,431
[45] Date of Patent: *Nov. 21, 2000

[54] AROMATIC MALEIMIDES AND METHODS OF USING THE SAME

[75] Inventors: Christopher W. Miller; Charles E. Hoyle, both of Hattiesburg, Miss.; E. Sonny Jönsson, Stockholm, Sweden

[73] Assignees: First Chemical Corporation, Pascagoula; Univ. of Southern Mississippi, Hattiesburg, both of Miss.

[ * ] Notice: This patent is subject to a terminal disclaimer.

[21] Appl. No.: 09/302,081

[22] Filed: Apr. 29, 1999

Related U.S. Application Data

[62] Division of application No. 09/084,519, May 26, 1998.
[60] Provisional application No. 60/047,729, May 27, 1997.

[51] Int. Cl.$^7$ .............................. C08F 2/50; C08F 18/14; C08F 20/18; C08F 22/40
[52] U.S. Cl. .......................... 522/167; 522/107; 522/181; 522/182; 522/178
[58] Field of Search ................................. 522/167, 168, 522/107, 141, 142, 181, 182, 178

[56] References Cited

U.S. PATENT DOCUMENTS

| | | |
|---|---|---|
| 3,129,225 | 4/1964 | Shapiro et al. . |
| 3,729,814 | 5/1973 | Wright et al. . |
| 3,850,955 | 11/1974 | Bublitz . |
| 3,890,270 | 6/1975 | Minieri et al. . |
| 4,287,294 | 9/1981 | Rubner et al. . |
| 4,329,556 | 5/1982 | Rubner et al. . |
| 4,416,975 | 11/1983 | Green et al. . |
| 4,544,621 | 10/1985 | Roth . |
| 4,626,497 | 12/1986 | Roth et al. . |
| 4,656,292 | 4/1987 | Roth . |
| 4,886,842 | 12/1989 | Drain et al. . |
| 5,171,655 | 12/1992 | Aoshima . |
| 5,196,550 | 3/1993 | Long, II et al. . |
| 5,319,101 | 6/1994 | Long, II et al. . |
| 5,446,073 | 8/1995 | Jonsson et al. . |
| 6,025,409 | 2/2000 | Jansen . |
| 6,034,150 | 3/2000 | Hoyle et al. . |

FOREIGN PATENT DOCUMENTS

| | | |
|---|---|---|
| 0 094 913 | 11/1983 | European Pat. Off. . |
| 0 318 893A | 6/1989 | European Pat. Off. . |
| 0 410 794 | 1/1991 | European Pat. Off. . |
| 4 024 710 | 2/1991 | Germany . |
| 3-084016 | 4/1991 | Japan . |
| 4-161413 | 6/1992 | Japan . |

OTHER PUBLICATIONS

Jonsson, S., et al., "Photochemistry of N–substituted Maleimides", pp. 377–387, 1995.
Woo–Sik Kim et al., "Synthesis and Photocrosslinking of Malemide–Type Polymers," Macromol. Rapid Commun., vol. 17, No. 11, pp. 835–841, Nov., 1996.
Chemical Abstracts, vol. 91, No. 6, Aug. 6, 1979, Columbus, Ohio, US; abstract No. 39958x, Shulyndin S.V. et al., "Synthesis and Properties of Polymers Containing Phosphorous and Nitrogen," p. 39962.
J. Put and F.C. DeSchryver, "Photochemistry of Nonconjugated Bichromophoric Systems. Intramolecular Photocycloaddition of N,N'–Alkylenedimaleimides in Solution," *J. Amer. Chem. Soc.*, 95, 140, Jan. 10, 1973.
F.C. DeSchryver, N. Boens and G. Smets, "Photopolymerization V. Unsensitized Solution Photocyclopolymerization of N,N'–Alkylenebismaleimides," *Journal of Polymer Science*, vol. 10, 1687–1699 (1972).

(List continued on next page.)

*Primary Examiner*—Susan W. Berman
*Attorney, Agent, or Firm*—Alston & Bird LLP

[57] ABSTRACT

Aromatic maleimides and methods using the same are disclosed. Polymerization of compositions which include the compounds of the invention may be activated by irradiating the composition with radiation.

11 Claims, 4 Drawing Sheets

OTHER PUBLICATIONS

F.C. DeSchryver, W.J. Feast and G. Smets, Photocycloaddition Polymerization. I. Preparation and Characterization of Poly–N,N'–polymethylenebisdichloromaleimides, *Journal of Polymer Science*, vol. 8, 1939–1948 (1970).

N. Boens, F.D. DeSchryver, and G. Smets, "Solid–State Ultraviolet Irradiation of Some Maleimides and Bismaleimides," *Journal of Polymer Science*, vol. 13, 201–213 (1975).

H. Zorr and H. Heusinger, "Intermediates of Radiation–Induced Polymerisation of Meleimides Studies by ESR," *European Polymer J.*, 14, 89 (1978).

Miller et al., *Polymer Preprints*, 38(2), 454–55 (1997).

Miller et al., *Polymer Preps*. 37(2), 346 (1996).

M. Yamada et al., *J. Polym. Sci.*, Part B, 6, 883 (1968).

F.C. DeSchryver et al., *J. Am. Chem. Soc.* 96, 6463:6469 (1974).

K. Meier et al., *J. Photochem.*, 35, 353–366 (1986).

Igarashi et al., Nippon Kagaku Kaishi (9), pp. 1616–1619 (Dec., 1989).

E.J. Corey et al., "Enantioselective total synthesis of Gracilins B and C using catalytic asymmetric Diels–Alder methodology," *Journal of the American Chemical Society*, vol. 117, No. 37, Sep. 20, 1995, pp. 9616–9617, XP002076382.

N.A. Kalinina et al., "Effect of maleic acid imides on rheological properties and radiation–induced three–dimensional polymerization of solid epoxy acrylate oligomer," *Russian Journal of Applied Chemistry*, vol. 70, No. 4, Apr. 1997, pp. 643–647, XP002076383.

Chemical Abstracts, vol. 79, No. 4, Jul. 30, 1973, Columbus, Ohio, US; abstract No. 19978c, S. Kristskaya et al., "Effect of maleimides on radiation vulcanization of cis–butadiene and butadiene–styrene rubbers," p. 65, XP002076384 see abstract & Kauch. Rezina, vol. 32, No. 3, 1973, pp. 21–22.

AROMATIC MALEIMIDES AND METHODS OF USING THE SAME

CROSS-REFERENCE TO RELATED APPLICATIONS

This application is a division of application Ser. No. 09/084,519, filed May 26, 1998, which is related to Provisional Application Serial No. 60/047,729, filed May 27, 1997, and claims the benefit of its filing date under 35 USC Section 119(e).

FIELD OF THE INVENTION

This invention relates to aromatic maleimide compounds and to methods for using the same.

BACKGROUND OF THE INVENTION

Ethylenically unsaturated compounds, such as acrylate derivatives, can be polymerized by exposure to radiation, typically ultraviolet light, in the presence of a photoinitiating system. Typically, the photoinitiating system includes (1) a compound capable of initiating polymerization of the ethylenically unsaturated compound upon exposure to radiation (a "photoinitiator") and optionally (2) a coinitiator or synergist, that is, a molecule which serves as a hydrogen atom donor. The coinitiators or synergists are typically alcohols, tertiary amines or ethers which have labile hydrogens attached to a carbon adjacent to a heteroatom.

Numerous photoinitiators with varying structures are commercially available for use in different systems. However, nearly all commercially available radiation curing processes require an initiator incorporated into the formulation, a large percent of which is not consumed. The use of conventional photoinitiators typically results in the production of small molecule photo-byproducts. The presence of the residual photo-active compounds and extractables can result degradation of the physical properties of the article, such as decreased light fastness, discoloration, and lower resistance to oxidative degradation. In addition, the residual photoinitiator can be extracted or leach out of the cured article or migrate to the surface of the article, which is undesirable in many applications.

Increasingly stringent environmental protection legislation has prompted the exploration and use of formulations which contain little or no volatile organic compounds (typically solvents). Thus the use of formulations with close to 100% reactive component is of great interest.

Aliphatic maleimides have been proposed as useful photoinitiators for the photopolymerization of acrylate systems via hydrogen abstraction mechanisms. However, prior attempts to provide aromatic maleimide compounds which photoinitiate via hydrogen abstraction mechanisms have been entirely unsuccessful.

SUMMARY OF THE INVENTION

The present invention is directed to N-aromatic maleimides useful in radiation curing of photopolymerizable compounds. Because the aromatic maleimides of the invention are capable of initiating photopolymerization of radiation curable compounds, the aromatic maleimides can replace conventional photoinitiators. The resultant photopolymerizable systems can be referred to generally as "photoinitiator-free systems."

In contrast to conventional photoinitiators, substantially all of the aromatic maleimide is consumed during initiation and photopolymerization. Thus, the aromatic maleimides of the invention can eliminate the problems associated with residual photoinitiator in the cured product, which are often observed with conventional photoinitiators. The aromatic maleimides of the invention can also minimize the need for solvent based systems.

The aromatic maleimides of the invention can be useful as photoinitiators in the photopolymerization of ethylenically unsaturated compounds, and in particular, acrylate derivatives. The aromatic maleimides of the invention can also be useful as comonomers with polymerizable compounds, such as vinyl ethers.

The N-aromatic maleimides of the invention are ortho-substituted (also referred to herein as "twisted") N-aromatic maleimides. In contrast to other aromatic maleimides, the imide ring is forced out of plane with respect to the phenyl ring. Although not wishing to be bound by any explanation of the invention, it is currently believed that the spatial orientation of the compounds of the invention contributes at least one part to the ability of the twisted aromatic maleimides (as compared to "non-twisted" aromatic maleimides) to initiate photopolymerization of photoinitiated photopolymerizable systems.

The ortho-substituted N-aromatic maleimide compounds of the invention have a structure according to Formula (I) below:

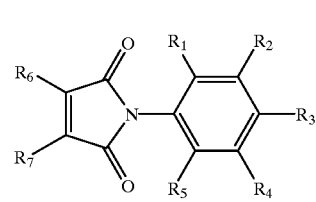

(I)

wherein:

$R_1$ is selected from the group consisting of $CX_3$, COOR, COR, OR, CN, SR, $N(R)_2$, $R_8$, X, and MI;

$R_2$, $R_3$, $R_4$, and $R_5$ are independently selected from the group consisting of H, $CX_3$, COOR, COR, OR, CN, SR, $N(R)_2$, $R_8$, X, and MI;

$R_6$ and $R_7$ are independently selected from the group consisting of H, lower alkyl, preferably $CH_3$, and halide, preferably chloride;

X is halide, preferably F, Cl, Br, or I;

R is selected from the group consisting of H, lower alkyl, cycloalkyl, and aryl;

$R_8$ is selected from the group consisting of lower alkyl, cycloalkyl, and aryl, or $R_8$ is a spacer group, preferably at the 2 position, connecting at least two compounds of Formula (I) to form a di- or multi-functional maleimide, said spacer group selected from the group consisting of:

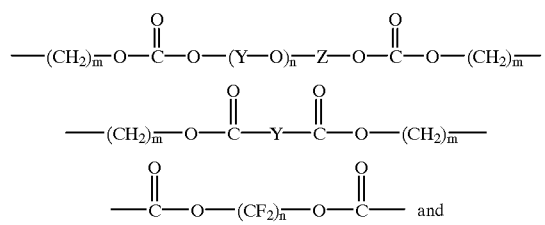

-continued

wherein Y and Z are each independently selected from C2 to C10 alkylene, m is an integer from 1 to 10, and n is an integer from 1 to 10; and MI is

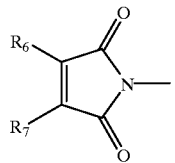

wherein $R_6$ and $R_7$ are as defined above.

The present invention also provides photopolymerizable compositions which include the compounds of Formula (I) above as a component thereof, and methods for the use of the compounds of Formula (I) in photopolymerization systems.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF THE INVENTION

Figure 1:
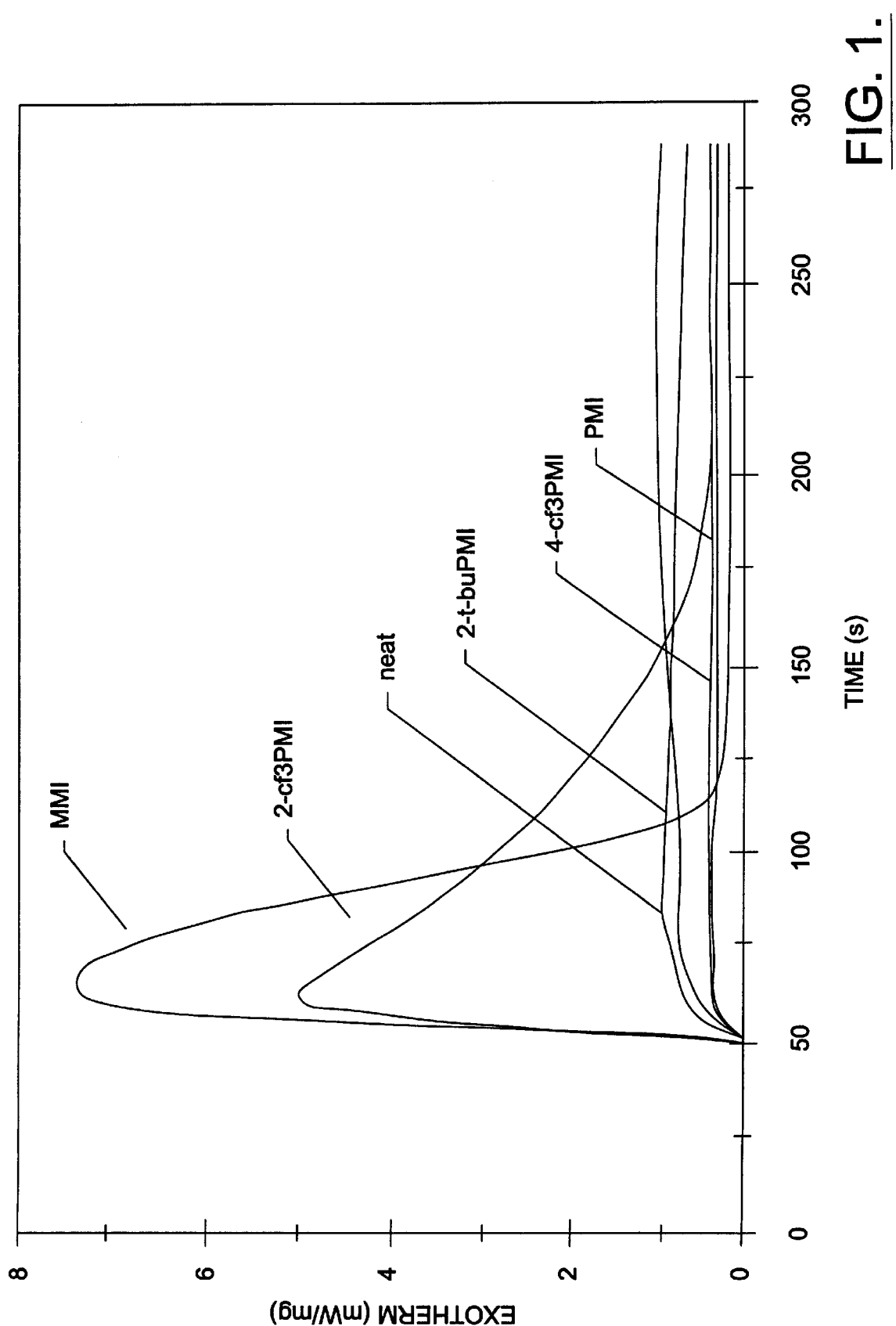
FIGS. 1 and 2 are graphs illustrating the results of a comparative example in which exemplary compounds of the invention are used to initiate polymerization of acrylates and demonstrate heat evolution (mW/mg and mW/mol for FIGS. 1 and 2, respectively) versus time of the photoinitiated photopolymerizations.

The aromatic maleimide compounds of the invention include compounds according to Formula (I) below:

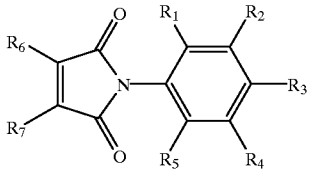

wherein:

$R_1$ is selected from the group consisting of $CX_3$, COOR, COR, OR, CN, SR, $N(R)_2$, $R_8$, X, and MI;

$R_2$, $R_3$, $R_4$, and $R_5$ are independently selected from the group consisting of H, $CX_3$, COOR, COR, OR, CN, SR, $N(R)_2$, $R_8$, X, and MI;

$R_6$ and $R_7$ are independently selected from the group consisting of H, lower alkyl, preferably $CH_3$, and halide, preferably chloride;

X is halide, preferably F, Cl, Br, or I;

R is selected from the group consisting of H, lower alkyl, cycloalkyl, and aryl;

$R_8$ is selected from the group consisting of lower alkyl, cycloalkyl, and aryl, or $R_8$ is a spacer group, preferably at the 2 position, connecting at least two compounds of Formula (I) to form a di- or multi-functional maleimide, said spacer group selected from the group consisting of:

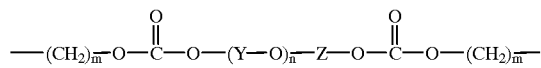

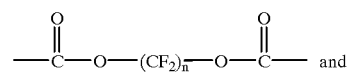

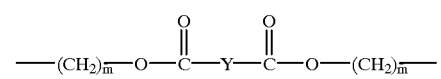

wherein Y and Z are each independently selected from C2 to $C_{10}$ alkylene, m is an integer from 1 to 10, and n is an integer from 1 to 10; and MI is

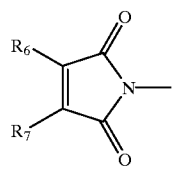

wherein $R_6$ and $R_7$ are as defined above.

In one embodiment of the invention, the compounds of Formula (I) include compounds in which $R_1$, is $CX_3$; each of $R_2$, $R_3$, $R_4$, $R_5$, and $R_7$ is hydrogen; and $R_6$ is H or lower alkyl. In another embodiment of the invention, the compounds includes those in which $R_1$ is lower alkyl; each of $R_2$, $R_3$, $R_4$, $R_5$ and $R_7$ is hydrogen; and $R_6$ is H or lower alkyl. In yet another embodiment of the invention, the compounds include those in which $R_1$ is halogen; each of $R_2$, $R_3$, $R_4$, $R_5$ and $R_7$ is hydrogen or $CX_3$; and $R_6$ is H or lower alkyl.

As used herein, the term "lower alkyl" refers to C1 to C10 straight chain or branched alkyl, such as methyl, ethyl, propyl, isopropyl, butyl, tert-butyl, sec-butyl, pentyl, hexyl, and the like. The term "cycloalkyl", refers to C3 to C10 cyclic alkyl, optionally substituted with lower alkyl. The term "aryl" refers to C6 to C10 cyclic aromatic groups, such as phenyl, naphthyl, and the like, optionally substituted with lower alkyl.

Exemplary aromatic maleimides of the invention include, but are not limited to, N-(2-$CF_3$-phenyl)maleimide (Ia)

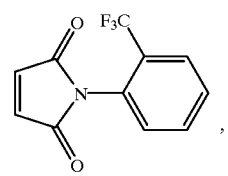

(Ia)

N-(2-t-butylphenyl)maleimide (Ib)

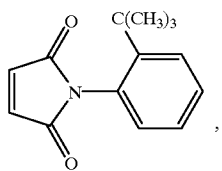

N-(2-CF$_3$-phenyl)methylmaleimide (Ic)

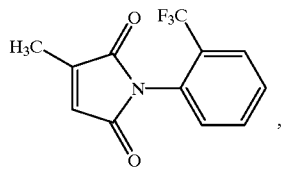

N-(2,4,6-isopropyl-3-maleimide phenyl)maleimide (Id)

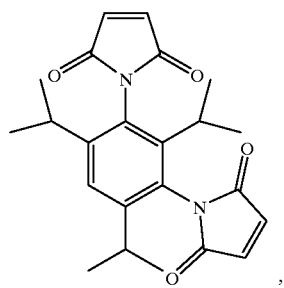

N-(2-iodo-phenyl)maleimide (Ie)

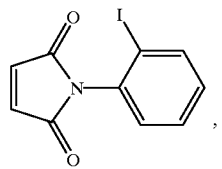

N-(2-bromo-3,5-CF$_3$-phenyl)maleimide (If)

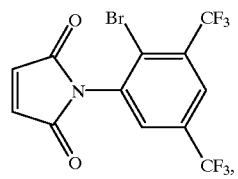

and the like.

Generally, aromatic maleimides of Formula (I) can be prepared using techniques known in the art, with slight modifications as noted herein. The compounds, for example, can be synthesized using a two step method, which begins with the reaction of a suitably substituted aromatic amine with maleic anhydride (or a substituted maleic anhydride, such as citraconic anhydride) in a polar solvent, such as diethylether, to produce the amic acid in near quantitative yields. The amic acid is then recovered from the solvent and residual solvent and water can be removed from the recovered product.

The second step is acid catalyzed ring closure to form the imide. This reaction is performed by dissolving the amic acid in a suitable solvent, such as an organic hydrocarbon solvent such as toluene, optionally with a small amount of cosolvent, such as dimethylsulfoxide (DMSO), adding a catalytic amount concentrated sulfuric acid, heating the mixture, preferably to reflux, and removing the water through the water/solvent azeotrope. Excess solvent can then be removed, and the residual concentrated solution of the imide in solvent precipitated. The imide is then collected and dried to remove water and residual solvent(s). The second step can also give near quantitative yields.

The present invention also provides photopolymerizable compositions which include an aromatic maleimide of Formula (I) as a component thereof, for example, a photoinitiator, a comonomer, and the like. As used herein, and as will be appreciated by the skilled artisan, the term photopolymerizable composition refers to compositions which harden or cure upon exposure to radiation.

Generally the compositions of the invention include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of radiation (ultraviolet or UV radiation, or radiation outside the UV spectrum). As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitriles. Suitable vinyl monomers include, but are not limited to, methyl acrylate, ethyl acrylate, tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, vinyl and vinylidene esters, vinyl and vinylidene ethers, vinyl and vinylidene ketones, butadiene, vinyl aromatics, i.e., styrene, alkyl styrenes, halostyrenes, alkoxystyrenes, divinyl benzenes, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

The photopolymerizable compound can be present in the compositions of the invention in amounts between about 0 and about 99.9 percent by weight based on the total weight of the composition, preferably between about 80 and about 99.9 percent by weight.

The aromatic maleimides of Formula (I), singly or as a mixture thereof, are useful as photopolymerization initiators. In this aspect of the invention, the compounds of Formula (I) are present in the photopolymerizable composition in an amount sufficient to initiate polymerization thereof upon exposure to radiation. The composition can include about 0.1 to about 20 percent by weight compound (I), based on the total weight of the photopolymerizable compounds.

The aromatic maleimides are particularly advantageous for use in "photoinitiator-free" systems, in which the aromatic maleimide(s) replace conventional photoinitiators. Although not wishing to be bound by any explanation of the invention, it is believed that the ortho substituted aromatic maleimides can initiate polymerization via hydrogen abstraction mechanisms, similar to that observed with aliphatic maleimides. This photoinitiation property is surprising, however, in view of observations that various aromatic maleimides do not initiate photopolymerizations. The aromatic maleimides of Formula (I) can also be used as photoinitiators and/or comonomers in donor/acceptor systems where the maleimide is an example of an acceptor and vinyl ethers and vinyl amides are examples of donors. Again, while not wishing to be bound by any explanation of the invention, it is currently believed that such photocopolymerization occurs via a charge transfer complex mechanism when the mixture is irradiated and initiation occurs via hydrogen abstraction of the excited N-arylmaleimide.

The photopolymerizable compositions of the invention may also contain other conventional agents, such as polymerization inhibitors, fillers, ultraviolet absorbers and organic peroxides. It can also be advantageous to also include as a component of the compositions of the invention a coinitiator or synergist, that is, a molecule which serves as a hydrogen atom donor or an electron donor. Coinitiators or synergists are known in the art, and are typically alcohols, tertiary amines or ethers which have available hydrogens attached to a carbon adjacent to a heteroatom. Such coinitiators are typically present in an amount between about 0.2 and about 25 percent by weight based on the total weight of the composition. Suitable compounds include, but are not limited to, triethanolamine, methyl-diethanolamine, ethyldiethanolamine and esters of dimethylamino benzoic acid. Other known coinitiators or accelerators can also be used. These compounds behave as coinitiators or accelerators for the primary photoinitiators and can increase the efficiency and speed of the polymerization process.

The photopolymerizable compositions can be applied or deposited on a surface of a substrate using conventional techniques and apparatus. The composition can be applied as a substantially continuous film. Alternatively, the composition can be applied in a discontinuous pattern. The thickness of the deposited composition can vary, depending upon the desired thickness of the resultant cured product.

Typically, the substrate is coated with the uncured photopolymerizable composition and passed under a commercially available UV or excimer lamp on a conveyer moving at predetermined speeds. The substrate to be coated can be, for example, metal, wood, mineral, glass, paper, plastic, fabric, ceramic, and the like.

The active energy beams used in accordance with the present invention may be visible light or ultraviolet light or may contain in their spectra both visible and ultraviolet light. The polymerization may be activated by irradiating the composition with ultraviolet light using any of the techniques known in the art for providing ultraviolet radiation, i.e., in the range of 200 nm and 450 nm ultraviolet radiation, and especially with the 308 nm emission from xenon chloride excimer lamps, commercially available from Fusion Systems, or by irradiating the composition with radiation outside of the ultraviolet spectrum. The radiation may be natural or artificial, monochromatic or polychromatic, incoherent or coherent and should be sufficiently intense to activate the photoinitiators of the invention and thus the polymerization. Conventional radiation sources include fluorescent lamps, excimer lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention.

The compositions are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The present invention will be further illustrated by the following non-limiting examples.

EXAMPLE 1

Preparation of N-(2-$CF_3$-phenyl)maleimide (Ia)

32.5 g of maleic anhydride is placed in 700 mL diethyl-ether and allowed to dissolve. 41.48 mL of 2-trifluoromethyl aniline is added squirtwise to the stirring solution. The reaction is allowed to proceed at room temperature overnight and a pale white precipitate is observed. The stirring solution is then warmed for several hours and filtered, yielding a pale white solid. The mother liquor is then combined with the wash liquor and allowed to stir again, and additional product is filtered off. The solids are then combined and dried in vacuum. Typical yields are 90–98%.

44.8 g of the maleamic acid is then placed in a three necked flask with 100 mL toluene and 25 mL DMSO, and allowed to dissolve. 1.8 mL of concentrated sulfuric acid is then added to the stirring mixture, which is then heated to about 130° C. The reaction mixture is allowed to reflux for 4 hours or until an azeotrope is no longer observed. Excess toluene is then removed via vacuum distillation. The mixture is then added to stirring distilled water to precipitate the imide and remove excess DMSO. The aqueous suspension is allowed to stir overnight and is then filtered. The pale white solid is then dried under vacuum to remove water, DMSO and toluene. Yields are typically 90–97%.

Products from both steps are analyzed using $^1H$ and $^{13}C$ NMR in $d_6$-DMSO. The maleamic acid is characterized by a broad peak due to the acid proton near 13–14 ppm, a peak due to the amide proton near 10 ppm, and two doublets due to the ene protons near 6.4 ppm in the proton spectra. The maleamic acid is also characterized by two peaks near 165 ppm due to the two carbonyls in the carbon spectrum. The maleimide is characterized by the absence of the acid and amide proton peaks, and the single ene proton peak shifted to near 7.6 ppm in the proton spectrum. In the carbon spectrum the maleimide shows a single carbonyl peak near 170 ppm.

The melting point of N-(2-$CF_3$-phenyl)maleimide is measured using DSC at a heating rate of 20° C./min and found to be 115.91° C. (endotherm peak maximum). Heat of fusion is also calculated to be 71.62 J/g.

EXAMPLE 2

Preparation of N-(2-t-butylphenyl)maleimide (Ib)

N-(2-t-butylphenyl)maleimide is prepared as described in Example 1, except substituting 2-trifluoromethyl aniline with 2-tert-butyl aniline. The melting point of N-(2-t-butylphenyl)maleimide is measured using DSC at a heating rate of 20° C./min and is found to be 99.64° C. (endotherm peak maxima). Heat of fusion is also calculated to be 94.02 J/g.

EXAMPLE 3

Preparation of N-(2-CF$_3$-phenyl)methylmaleimide (Ic)

N-(2-CF$_3$-phenyl)maleimide is also prepared as described in Example 1, except substituting citraconic anhydride for maleic anhydride.

EXAMPLE 4

Preparation of N-(2-iodo-phenyl)maleimide (Ie)

N-(2-iodo-phenyl)maleimide is prepared as described in Example 1, except substituting 2-trifluoromethyl aniline with 2-iodoaniline.

EXAMPLE 5

Preparation of N-(2-bromo-3,5-CF$_3$-phenyl) maleimide (If)

N-(2-bromo-3,5-CF$_3$-phenyl)maleimide is prepared as described in Example 1, except substituting 2-trifluoromethyl aniline with 2-bromo-3,5-trifluoromethyl aniline.

EXAMPLE 6

Use of Aromatic Maleimides as Photoinitiators

Figure 2:
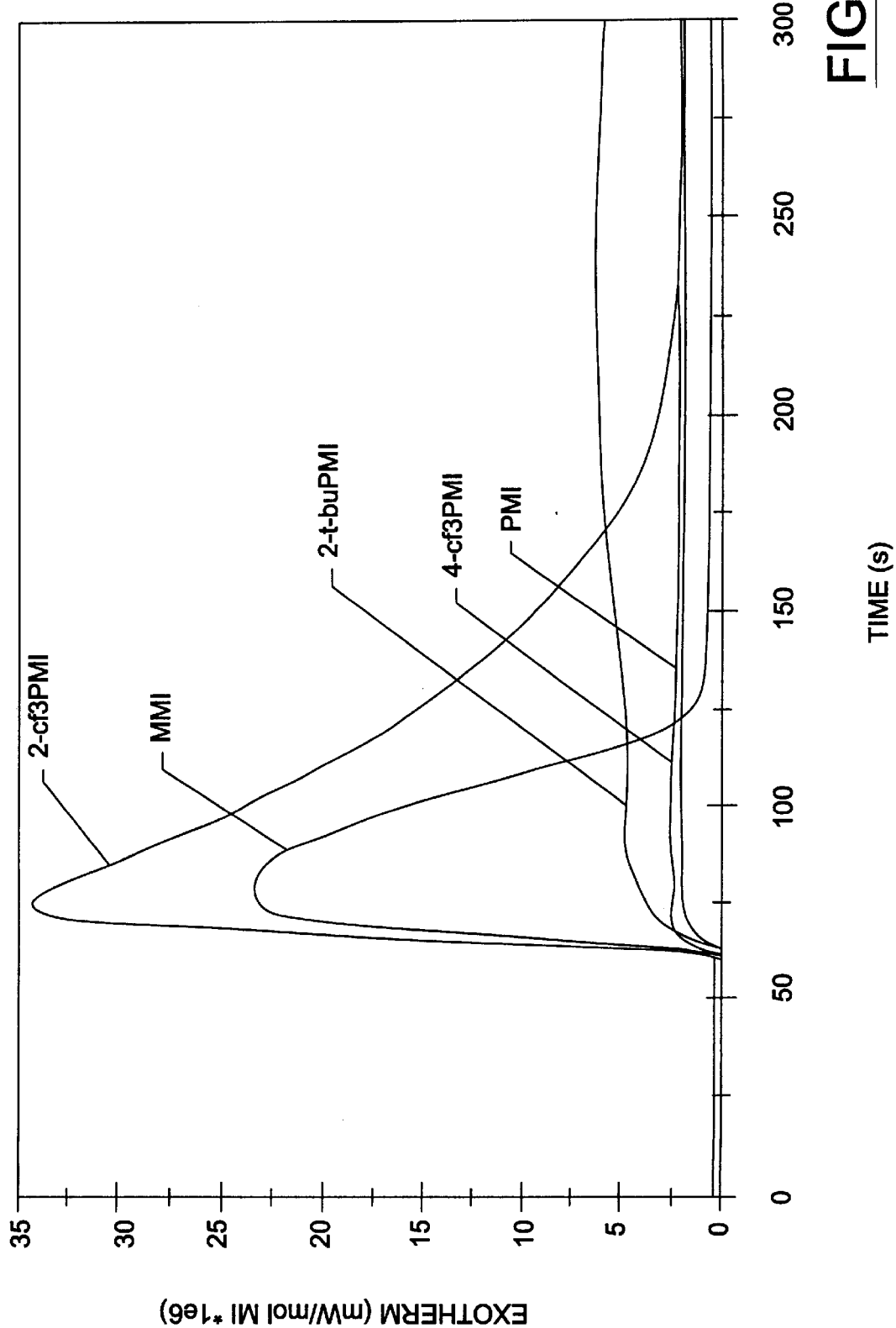

FIGS. 1 and 2 are graphs illustrating the results of a comparative example in which exemplary compounds of the invention are used to initiate polymerization of acrylates and demonstrate heat evolution (mW/mg and mW/mol for FIGS. 1 and 2, respectively) versus time of the photoinitiated photopolymerizations. Specifically, solutions of 3.5 % (weight) maleimide in fresh PEG400 diacrylate (inhibited with 400–600 ppm MHQ) are prepared. PEG refers to polyethylene glycol, and MHQ refers to methylhydroquinone. PEG400 diacrylate (PEG400 DA) is commercially available from Aldrich Chemical Co. N-(2-CF$_3$-phenyl) maleimide (2-cf3PMI) and N-(2-t-butylphenyl)maleimide (2-t-buPMI), as well as N-methylmaleimide (MMI), N-(4-trifluoromethylphenyl)maleimide (4-CF$_3$PMI), N-(4-cyanophenyl)maleimide (4-CNPMI) and N-phenylmaleimide (PMI) are compared. Photopolymerizations are carried out on a Perkin-Elmer DSC-7, modified by the addition of a medium pressure mercury lamp source and quartz windows in the sample cover. Polymerizations are performed in nitrogen after a 5 minute purge time with an on sample light intensity of about 28 mW/cm$_2$. The exotherm peak maximum is proportional to the maximum rate of polymerization and the time to peak maximum is related to the overall efficiency of the initiation reaction.

The data may be compared in two ways: efficiency by weight percentage and efficiency per mole of initiator chromophore (maleimide). The 4-CF$_3$PMI, PMI and 4-CNPMI solutions show efficiencies of polymerization lower than that of neat PEG400DA (1 mW/mg). On a weight percent basis, 2-t-buPMI is only very slightly more efficient that PEG400DA, while 2-cf3PMI is 5 times more efficient the PEG400DA. This is to be compared to the efficiency shown by a typical aliphatic maleimide MMI which is about 7.5 times more efficient than neat PEG400DA. It is noted that the time to peak maximum is slightly shorter for the 2-cf3PMI than for MMI. When the data are normalized to efficiency per mole of initiator chromophore (maleimide), however, it is seen that 2-cf3PMI is approximately 1.5 times more efficient than MMI, and should be comparable in initiating efficiency to the more reactive aliphatic maleimides. As noted above, sample DSC curves are illustrated in FIGS. 1 and 2.

Figure 3:
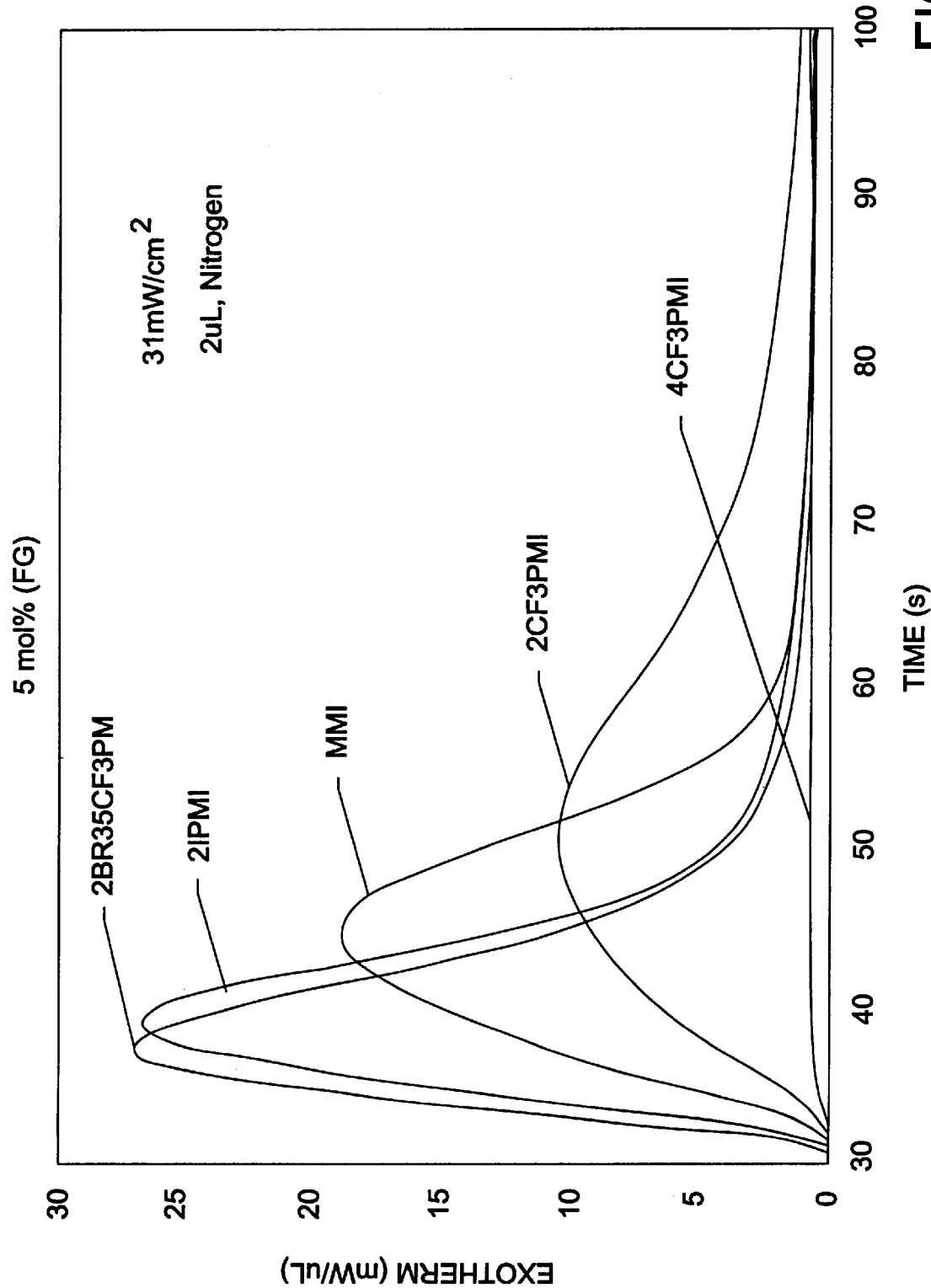
FIGS. 3 and 4 are graphs illustrating the results of another comparative example in which exemplary compounds of the invention are used to initiate polymerization of acrylates and demonstrate heat evolution (mW/mL) versus time of the photoinitiated photopolymerizations.
Figure 4:
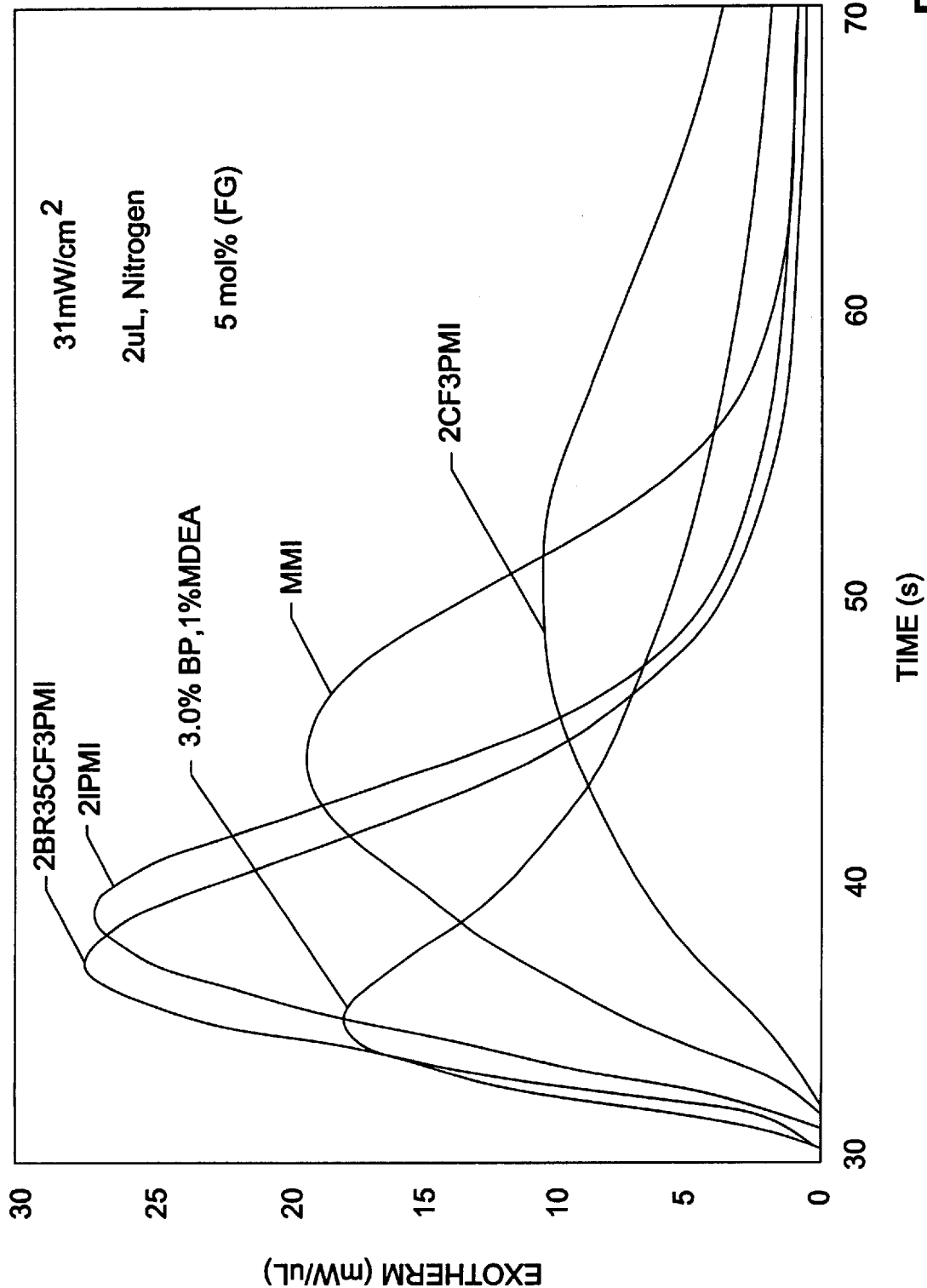

FIGS. 3 and 4 are graphs illustrating the results of another comparative example in which exemplary compounds of the invention are used to initiate polymerization of acrylates and demonstrate heat evolution (mW/mL) versus time of the photoinitiated photopolymerizations. Solutions of maleimide in fresh PEG400DA as described above are prepared. 2-BR35CF3PM and 2IPMI refer to N-(2-bromo-3,5-trifluoromethyl-phenyl)maleimide and N-(2-iodo-phenyl) maleimide, respectively. 2CF3PMI, MMI, and 4CF3PMI have the meanings described above. Photopolymerizations are carried out as described above, except with an on sample light intensity of about 31 mW/cm$_2$.

FIG. 3 compares the exotherms observed for several "twisted" aromatic maleimides to those observed for an alkyl maleimide MMI and a non-twisted aromatic maleimide (4CF3PMI). As indicated, the non-twisted aromatic maleimide 4CF3PMI did not initiate polymerization. 2BR35CF3PMI and 2IPMI show enhanced reactivity even as compared to MMI. FIG. 4 compares polymerization efficiency with the above noted maleimides and with a conventional initiator system (3 wt. % benzophenone (BP) with 1 wt. % amine (MDEA)). As demonstrated in FIG. 4, 2BR35CF3PMI and 2IPMI initiate more efficiently under these conditions that benzophenone with amine.

In summary, initiation of PEG400DA diacrylate polymerization is demonstrated with ortho-substituted ("twisted") aromatic maleimides. In particular, the 2-CF3PMI shows initiation efficiency per mole of maleimide greater than that for MMI, and 2BR35CF3PMI and 2IPMI show improved efficiency as compared to the aliphatic maleimide MMI and a conventional benzophenone/amine system.

Although not wishing to be bound by any explanation of the invention, it is believed that two effects contribute to the result: the steric considerations which force the imide ring out of plane with respect to the phenyl ring; and the electron withdrawing nature of the substituent.

Single crystal X-ray diffraction experiments were conducted on crystalline samples of several of the twisted aromatic maleimides to examine the spatial relationship of the phenyl ring to the maleimide ring of the ortho-substituted aromatic maleimides. These experiments confirmed the "twisted" configuration of the maleimides of the invention, i.e., that the phenyl ring is out of the plane with respect to the maleimide ring. The torsion angle between the two rings was typically somewhere between about 88 and 93 degrees, depending upon the compound.

The foregoing examples are illustrative of the present invention and are not to be construed as limiting thereof.

That which is claimed is:

1. A photopolymerizable composition comprising a photopolymerizable compound comprising at least one ethylenically unsaturated double bond and a photoinitiator comprising an ortho-substituted N-aromatic maleimide of the Formula (I)

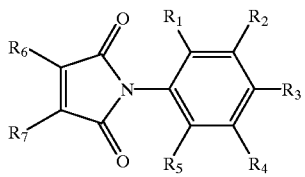

wherein:

$R_1$ is selected from the group consisting of $CX_3$, COOR, COR, CN, SR, $N(R)_2$, $R_8$, X, and MI;

$R_2$, $R_3$, $R_4$, and $R_5$ are independently selected from the group consisting of H, $CX_3$, COOR, COR, OR, CN, SR, $N(R)_2$, $R_8$, X, and MI;

$R_6$ and $R_7$ are independently selected from the group consisting of H, lower alkyl, and halide;

X is halide with the proviso that when $R_1$ is halide, at least one of $R_2$, $R_3$, $R_4$, and $R_5$ is $CX_3$, COOR, COR, OR, CN, SR, $N(R)_2$, or MI;

R is selected from the group consisting of H, lower alkyl, cycloalkyl, and aryl;

$R_8$ is selected from the group consisting of lower alkyl, cycloalkyl, and aryl, with the proviso that when $R_1$ is lower alkyl, at least one of $R_2$, $R_3$, $R_4$, and $R_5$ is $CX_3$, COOR, COR, OR, CN, SR, $N(R)_2$, or MI and further $R_1$ is not benzyl, or $R_8$ is a spacer group connecting at least two compounds of Formula (I) to form a di- or multi-functional maleimide, said spacer group selected from the group consisting of:

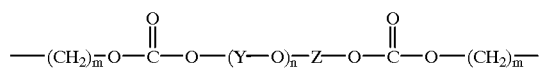

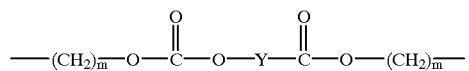

and

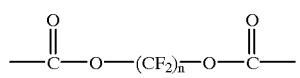

wherein Y and Z are each independently selected from C2 to C10 alkylene, m is an integer from 1 to 10, and n is an integer from 1 to 10; and MI is

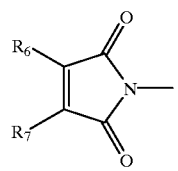

wherein $R_6$ and $R_7$ are as defined above.

2. The composition of claim 1, wherein $R_1$ is $CX_3$; each of $R_2$, $R_3$, $R_4$, and $R_5$ is hydrogen; and each of $R_6$ and $R_7$ is H or lower alkyl.

3. The composition of claim 1, wherein $R_1$ is lower alkyl; at least one of $R_2$, $R_3$, $R_4$, and $R_5$ is MI; and each of $R_6$ and $R_7$ is hydrogen or lower alkyl.

4. The composition of claim 1, wherein $R_1$ is halogen; at least one of $R_2$, $R_3$, $R_4$, and $R_5$ is $CX_3$; and each of $R_6$ and $R_7$ is H or lower alkyl.

5. The composition of claim 1, wherein said compound is selected from the group consisting of N-(2-$CF_3$-phenyl) maleimide, N-(2-$CF_3$-methylphenyl)maleimide, N-(2,4,6-isopropyl-3-maleimide phenyl)maleimide, and N-(2-bromo-3,5-$CF_3$-phenyl)maleimide.

6. A method of polymerizing a polymerizable compound comprising at least one ethylenically unsaturated double bond, comprising exposing said compound to radiation in the presence of a photoinitiator comprising an ortho-substituted N-aromatic maleimide.

7. The method of claim 6, wherein said ortho-substituted N-aromatic maleimide has the Formula (I)

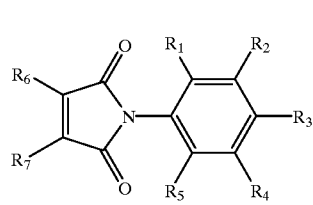

wherein:

$R_1$ is selected from the group consisting of $CX_3$, COOR, COR, OR, CN, SR, $N(R)_2$, $R_8$, X, and MI;

$R_2$, $R_3$, $R_4$, and $R_5$ are independently selected from the group consisting of H, $CX_3$, COOR, COR, OR, CN, SR, $N(R)_2$, $R_8$, X, and MI;

$R_6$ and $R_7$ are independently selected from the group consisting of H, lower alkyl, and halide;

X is halide;

R is selected from the group consisting of H, lower alkyl, cycloalkyl, and aryl;

$R_8$ is selected from the group consisting of lower alkyl, cycloalkyl, and aryl, or $R_8$ is a spacer group connecting at least two compounds of Formula (I) to form a di- or multi-functional maleimide, said spacer group selected from the group consisting of:

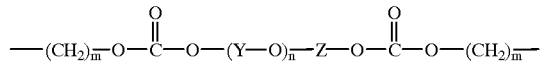

-continued

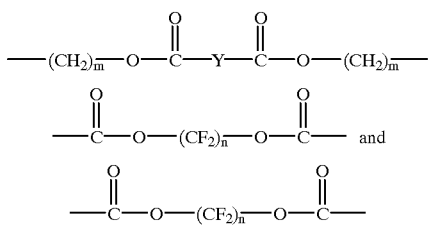

wherein Y and Z are each independently selected from C2 to C10 alkylene, m is an integer from 1 to 10, and n is an integer from 1 to 10; and MI is

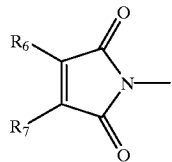

wherein $R_6$ and $R_7$ are as defined above.

8. The method of claim 7, wherein $R_1$ is $CX_3$; each of $R_2$, $R_3$, $R_4$, and $R_5$ is hydrogen; and each of $R_6$ and $R_7$ is H or lower alkyl.

9. The method of claim 7, wherein $R_1$ is lower alkyl; each of $R_2$, $R_3$, $R_4$, and $R_5$ is selected from the group consisting of hydrogen, lower alkyl and MI; and each of $R_6$ and $R_7$ is H or lower alkyl.

10. The method of claim 7, wherein $R_1$ is halogen; each of $R_2$, $R_3$, $R_4$, and $R_5$ is selected from the group consisting of hydrogen and $CX_3$; and each of $R_6$ and $R_7$ is H or lower alkyl.

11. The method of claim 7, wherein said compound is selected from the group consisting of N-(2-$CF_3$-phenyl) maleimide, N-(2-t-butylphenyl)maleimide, N-(2-$CF_3$-methylphenyl)maleimide, N-(2,4,6-isopropyl-3-maleimide phenyl)maleimide, N-(2-iodo-phenyl)maleimide, and N-(2-bromo-3,5-$CF_3$-phenyl)maleimide.

* * * * *